United States Patent [19]
DeVito et al.

[11] Patent Number: 5,757,006
[45] Date of Patent: May 26, 1998

[54] ARTICULATING DETECTOR ARRAY FOR A GAMMA CAMERA

[75] Inventors: Raymond P. DeVito, Palatine; James J. Hamill, Elgin, both of Ill.

[73] Assignee: Siemens Medical Systems, Inc., Iselin, N.J.

[21] Appl. No.: 790,833

[22] Filed: Jan. 30, 1997

[51] Int. Cl.$^6$ .................................................. G01T 1/161
[52] U.S. Cl. ................ 250/366; 250/363.04; 250/370.09
[58] Field of Search .......................... 250/363.04, 363.1, 250/366, 370.09, 370.11, 370.13; 378/98.8

[56] References Cited

U.S. PATENT DOCUMENTS

| | | | |
|---|---|---|---|
| 4,070,581 | 1/1978 | Gibbons et al. | 250/370.11 X |
| 4,417,354 | 11/1983 | Pfeiler | 378/19 |
| 5,391,882 | 2/1995 | Rhiger | 250/370.13 |

*Primary Examiner*—Edward J. Glick
*Attorney, Agent, or Firm*—Mark H. Jay

[57] ABSTRACT

An articulating detector array for gamma cameras is disclosed which is adaptable to perform different imaging techniques in a single apparatus. The articulating detector array is adapted to detect incident gamma radiation from diverse directions as well as Compton scattering thereof without the need of a collimator, as so has improved gamma ray detection efficiency. The detector array includes radiation detectors in an array and movable to a plurality of positions, in which each radiation detector is responsive to gamma radiation from a target for generating detection signals for use in tomographic imaging of the source. The detector array includes articulating support structures for mounting the detectors to the base and for moving the detectors from a first position to a second position. In one embodiment, the articulating support structures includes a first portion connected to a detector; and a second portion connected to the base, in which the first portion is adapted to extend from the second portion from the first position to the second position. In another embodiment, the articulating support structures include a pivot for pivotably mounting the detectors and for rotating the detectors from a first position to a second position.

12 Claims, 3 Drawing Sheets

5,757,006

ARTICULATING DETECTOR ARRAY FOR A GAMMA CAMERA

BACKGROUND INFORMATION

1. Technical Field

This disclosure relates to tomographic imaging, and in particular to an articulating detector array for improved gamma ray detection in a gamma camera.

2. Description of the Related Art

In conventional gamma cameras such as Anger cameras known in the art, a single detector having a planar surface is typically employed for detecting gamma rays for tomographic imaging. FIG. 1 is a schematic drawing of a detector system 10 in the prior art, having a crystal 12 for converting gamma radiation to visible light for input to a plurality of photomultiplier tubes (PMTs) 14. The crystal 12 and PMTs 14 are typically mounted in shielding 16 to prevent stray gamma rays from being detected; for example, from lateral directions away from the target, and thus affecting the imaging.

A collimator 18 may be used to collimate incident gamma rays 20, such as gamma rays with energies of about 140 keV, from a variety of angles of incidence into a set of collimated rays 22.

Some detectors are adapted to detect photons which have experienced Compton interaction, in which emitted photons transfer part of their energy to free electrons. The original photons are scattered in a new direction with reduced energy that is dependent on the scatter angle. By measuring the energy of the primary electrons and the energy and direction of scatter of received photons, gamma cameras may employ kinematic techniques to perform imaging from the Compton scattered radiation.

Heretofore, such gamma cameras in the prior art have typically been implemented for the single type of imaging technique using collimation. For example, the gamma camera 10 in FIG. 1 may be provided with a single detector with a single detector head for planar imaging of gamma rays or single-photon emission computed tomography (SPECT). With such a structure, the gamma camera 10 cannot be used for Compton scatter imaging, since Compton scatter imaging requires two or more detectors for imaging. Substantial reconfiguration of the gamma camera 10 would be required to use a single headed detector with other single headed detectors to perform Compton scatter imaging.

With such limitations, gamma cameras in the prior art have not been adaptable to perform different imaging techniques. Since gamma cameras for each type of imaging (for example, SPECT or Compton scatter imaging) are expensive, the lack of adaptability has prevented the widespread use of different imaging techniques which, in conjunction, may complement the overall imaging of a patient.

A need exists for a gamma camera which is adaptable to perform different imaging techniques in a single apparatus.

In prior art imaging, collimators and photomultiplier tubes are typically required for detecting low energy gamma rays, since the planar arrangement of the detectors typically limits the detecting ability of the gamma camera; for example, to detect Compton scattering of incident gamma rays. With a collimator, all but about 1 gamma ray per $10^4$ are precluded from detection. The use of collimators and photomultiplier tubes is also generally limited in the directions from which the incident gamma rays are detected.

A need exists for a gamma camera adapted to detect incident gamma rays from diverse directions as well as adapted to utilize the kinematics of Compton scattering to obtain directional information of the gamma rays without the need of a collimator.

SUMMARY

An articulating detector array for gamma cameras is disclosed which is adaptable to perform different imaging techniques in a single apparatus. The articulating detector array is adapted to detect incident gamma rays from diverse directions as well as Compton scattering thereof without the need of a collimator, as so has improved gamma ray detection efficiency.

The detector array includes a plurality of radiation detectors each mounted in an array with each radiation detector being movable to a plurality of positions, in which each radiation detector is responsive to gamma radiation from a source for generating corresponding detection signals for use in tomographic imaging of the source. The detector array includes a base and a plurality of articulating support structures each mounting a corresponding one of the plurality of detectors to the base and for moving the corresponding detector from a first position to a second position.

In one embodiment, each of the plurality of articulating support structures includes a first portion connected to a corresponding detector; and a second portion connected to the base, in which the first portion is adapted to extend from the second portion from the first position to the second position.

In another embodiment, each of the plurality articulating support structures includes a corresponding pivot for pivotably mounting a corresponding one of the plurality of detectors to the corresponding support structure and for rotating the corresponding detector from a first position to a second position.

BRIEF DESCRIPTION OF THE DRAWINGS

The features of the disclosed articulating detector array will become more readily apparent and may be better understood by referring to the following detailed description of illustrative embodiments of the present invention, taken in conjunction with the accompanying drawings, in which.

DESCRIPTION OF THE PREFERRED EMBODIMENTS

Figure 1:
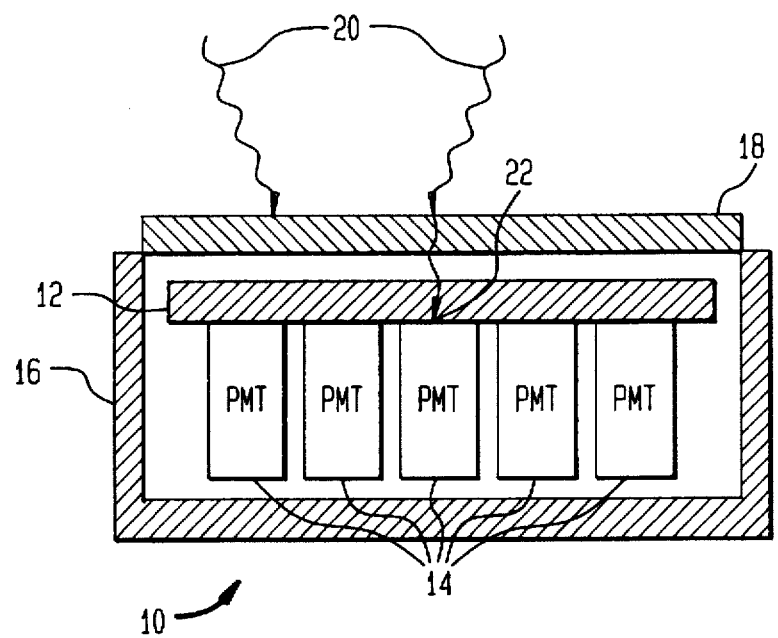
FIG. 1 is a schematic drawing of a detector system in the prior art.
Figure 2:
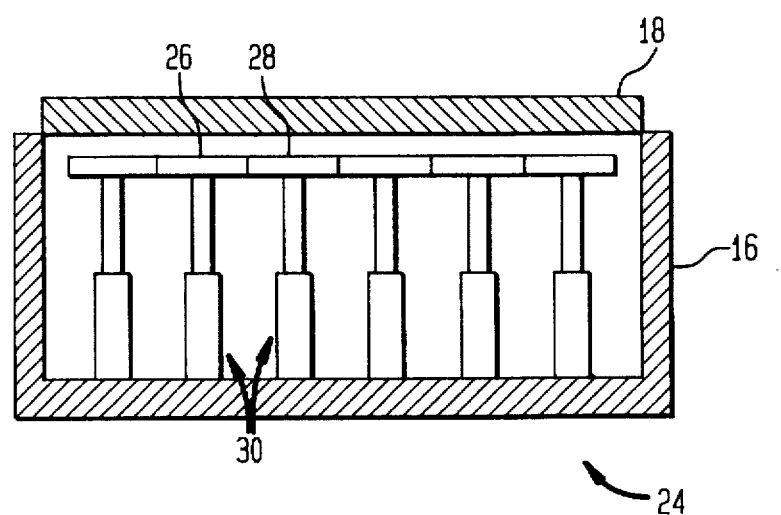
FIG. 2 is a schematic drawing of the disclosed articulating detector array for use with a collimator.

Referring now in specific detail to the drawings, with like reference numerals identifying similar or identical elements, as shown in FIGS. 2–6, an articulating detector array is disclosed for use in a gamma camera. As shown in FIG. 2, the disclosed articulating detector array 24 includes a plurality of detectors 26, 28 each positioned within a housing which may include the shielding 16, with the detectors 26, 28 mounted on corresponding supporting structures, such as posts 30. In an illustrative embodiment, each of the plurality of detectors 26, 28 is a solid state detector module, such as semiconductor detectors, mounted in an array to substantially span the length and breadth of the housing. For example, the detectors 26, 28 may be composed of cadmium telluride (CdTe) or cadmium zinc telluride (CZT or CdZnTe), which are on the order of several centimeters in length and width and are pixelated into distinct pixels of approximately 1 mm. to 3 mm. on each side. Such semiconductor-based detectors operate routinely at temperatures up to 30° C. without excessive thermal noise.

Each detecting surface of the detectors 26, 28 is adapted to receive incident uncollimated gamma rays, or alternatively gamma rays collimated by a collimator 18 positioned above the detectors 26, 28. Such an array 32 of detectors 26, 28 may be used for detecting low energy gamma rays; for example, gamma rays having energies less than about 200 keV.

Figure 3:
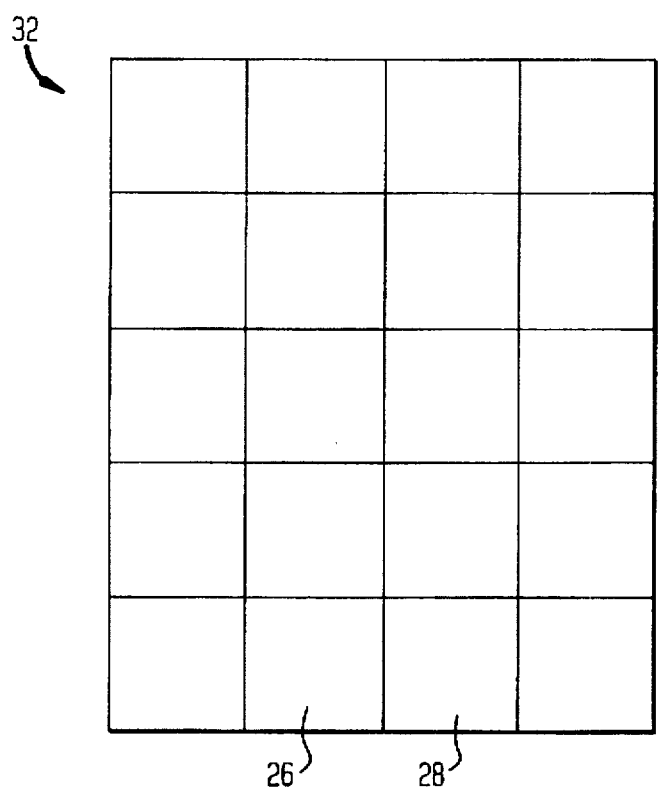
FIG. 3 is a schematic drawing of a top view of the disclosed articulating detector array of FIG. 2.

In an illustrative embodiment, each of the plurality of detectors 26, 28, shown in a side view in FIG. 2, has a substantially planar detector surface, and so the plurality of detectors 26, 28, in a tiling arrangement, present a substantially contiguous planar detector surface 32, as shown in the top view in FIG. 3, for receiving incident gamma rays.

Each detector 26, 28 may have, for example, a single detector surface, or may be composed of multiple detector modules, such as four detector modules by four detector modules to present a 4×4 square of detector surfaces. It is understood that the detectors 26, 28 may have substantially square detector surfaces, as shown in FIG. 3, to substantially span the length and width of the housing, or may have detector surfaces of any shape which may span the length and width of the housing. Each detector module surface may be about 40 mm.×40 mm. Multiple detectors 26, 28 may be used to provide an array of, for example, 200 detector modules in groups of 10 to provide an overall detector surface of, for example, about 16 in.×20 in. It is understood that the relatively small detection surface area allows arrays having smaller dimensions to be implemented.

In other embodiments, each of the plurality of detectors 26, 28 may be oriented on the corresponding posts 30 to present a substantially contiguous detector surface approximating a curved surface. Alternatively, each of the plurality of detectors 26, 28 may have a curved detector surface such that the plurality of detectors 26, 28 present a substantially contiguous detector surface approximating a curved surface.

With either a planar or curved detector surface presented by the array 32 of detectors 26, 28 as well as a collimator 18 positioned above the detector surface of the detectors 26, 28, as needed, the gamma camera may be used for conventional nuclear medicine imaging. For example, the entire gamma camera may be rotated around a target with the detector surface of the gamma camera presented toward the target for performing SPECT imaging.

In an alternative embodiment, the posts 30 of FIG. 2 may be adapted to selectively re-position the detectors 26, 28 within the housing for use in a Compton camera mode for applying Compton scattering detection techniques to register Compton scatter vertices and energies for image construction. Coincidence electronics known in the art are used to identify and measure coincidence events between different detectors in the neighborhood of a potential scatter event.

Figure 4:
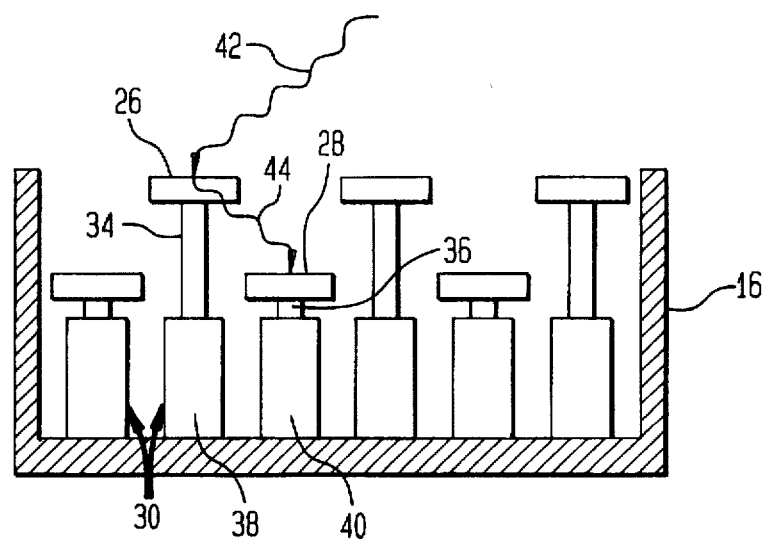
FIG. 4 is a schematic drawing of a side view of the disclosed articulating detector array for use in a Compton camera mode.

For example, as shown in a side view in FIG. 4, with no collimator positioned above the detectors 26, 28, the posts 30 may be selectively retractable; for example, each of detectors 26, 28 may be disposed upon a corresponding first portion 34, 36, which is selectively retractable within a corresponding second portion 38, 40 in a telescoping arrangement to allow each individual detector to move from a flat detector position in a vertical direction relative to the base of the corresponding posts 30. Alternatively, the first portions 34, 36 may slidably engage the corresponding second portions 38, 40.

As shown in FIG. 4, the detectors 26, 28 may be positioned, for example, in an alternating embodiment, with the first portion 34 extending from its corresponding second portion 38 to support the detector 26 in a raised position, and the first portion 36 of the detector 28 retracted into its corresponding second portion 40 such that the detector 28 has a height lower than the detector 26. In such an embodiment, detector areas of a portion of the plurality of detectors 26, 28 are relatively exposed to each other.

With alternating raised and lowered detectors as shown in FIG. 4, an incident gamma ray 42 detected by the detector 26 may be scattered by Compton scattering, with the detector 28 positioned such that the scattered gamma ray 44 may be detected by the detector 28 to provide improved detection sensitivity. For example, gamma ray energies above about 200 keV may be detected, and since a collimator is not required, a large fraction of all incident gamma rays may be detected.

Such an alternating detector may be used for PET imaging, in which radiation from positron emitting isotopes may be detected in a Compton scatter mode using cross detector head coincidence measurements between two or more detector heads of the detectors 26, 28.

The detectors 26, 28 shown in the side view in FIG. 4 may also present a substantially contiguous planar detector surface 32, as shown in the top view in FIG. 3, for receiving incident gamma rays.

Using the corresponding heights of the various detectors 26, 28 above the base, the imaging of the target may be determined using tomographic imaging techniques known in the art.

Figure 5:
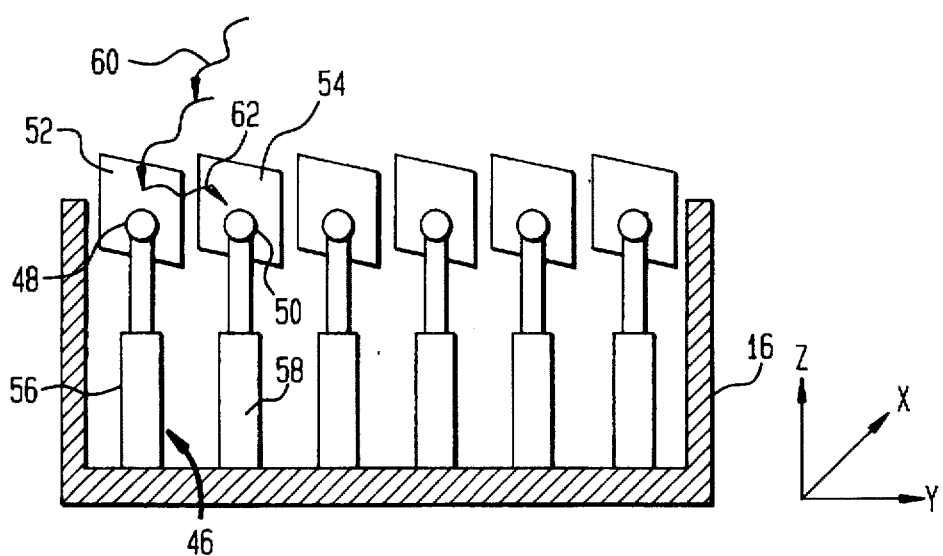
FIG. 5 is a schematic drawing of a side view of an alternative embodiment of the disclosed articulating detector array for use in a Compton camera mode.

In another illustrative embodiment, as shown in FIG. 5, the support structures may include rotation mechanisms for rotatably orienting and/or pivoting the detector in at least one dimension. For example, using an x-y-z coordinate axis as a reference system, the post 46 may include motorized mechanisms 48, 50 for pivotably mounting corresponding detectors 52, 54 to corresponding support structures 56, 58. The motorized mechanisms 48, 50 may be operated by control circuits (not shown in FIG. 5) known in the art for rotating the corresponding detectors 52, 54 independently or in unison; for example, each of the detectors 52, 54 may be rotated about 45° with respect to the x-axis and about 45° with respect to the y-axis. Accordingly, such rotatably oriented detectors operate in a Compton camera mode, in which an incident gamma ray 60 is detected by a first detector 52, from which a scattered gamma ray 62 is generated, which may be detected by the second detector 54.

Figure 6:
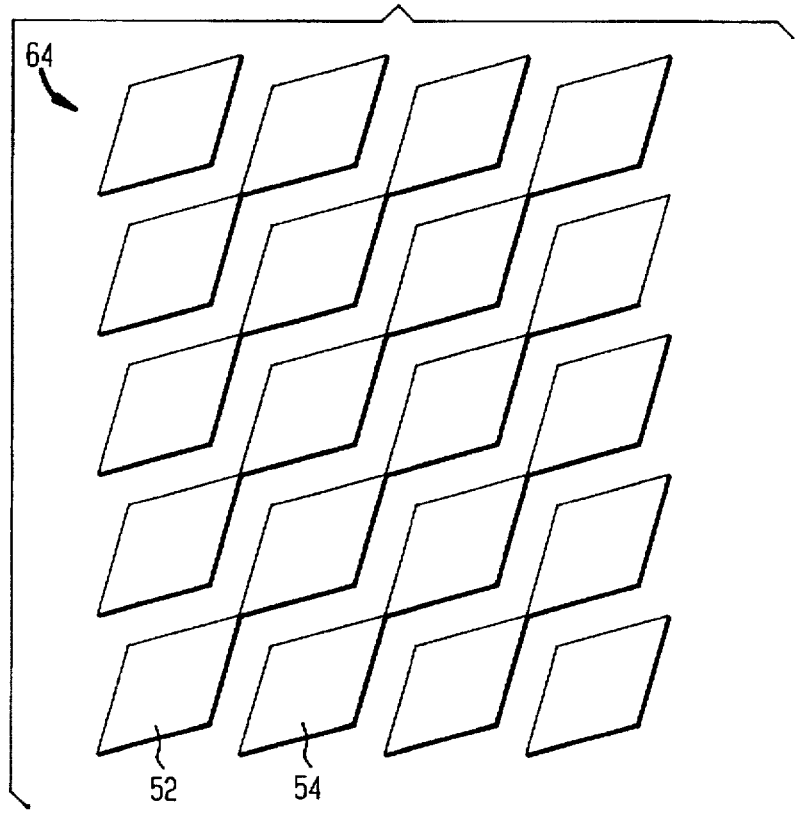
FIG. 6 is a schematic drawing of a top view of the disclosed articulating detector array of FIG. 5.

As shown in the top view in FIG. 6, with such detectors 52, 54 rotated, the array 64 of detectors may provide less detection aspect compared to the array 44 shown in FIG. 3, but provides for more diverse detector surfaces which are adapted for improved detection techniques using, for example, Compton scattering, as described above for FIG. 5.

According to another illustrative embodiment, with the detectors 52, 54 pivoted, the support structures 56, 58 may also be extended or retracted as described above for FIG. 2, such that the detectors 52, 54 may be oriented in a plurality of structures and angular orientations for optimal detection.

While the disclosed tomographic camera and method of use have been particularly shown and described with reference to the preferred embodiments, it is understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A detector array comprising:

a plurality of radiation detectors each being mounted in an array with each radiation detector being movable to a plurality of positions, wherein each radiation detector is responsive to gamma radiation from a target for generating corresponding detection signals for use in tomographic imaging of the target;

a base; and a plurality of articulating support structures, each for mounting a corresponding one of the plurality of radiation detectors to the base and for moving the corresponding radiation detector from a first position to a second position.

2. The detector array of claim 1 wherein each of the plurality of articulating support structures further includes:

a first portion connected to a corresponding radiation detector; and a second portion connected to the base, wherein the first portion extends from the second portion from the first position to the second position.

3. The detector array of claim 2 wherein each first portion and each corresponding second portion is connected in a telescoping orientation.

4. The detector array of claim 1 wherein the plurality of radiation detectors include:

a first set of radiation detectors in the first position for detecting incident gamma radiation and for scattering the incident gamma radiation by Compton scattering; and a second set of radiation detectors in a second position, wherein the second set of radiation detectors are positioned to detect the scattered gamma radiation.

5. The detector array of claim 1 wherein each of the plurality of articulating support structures includes a corresponding pivot for pivotably mounting a corresponding one of the plurality of radiation detectors to the corresponding support structure and for rotating the corresponding radiation detector from the first position to the second position.

6. The detector array of claim 5 wherein the plurality of radiation detectors includes:

a first set of radiation detectors in the first position for detecting incident gamma radiation and for scattering the incident gamma radiation by Compton scattering; and a second set of radiation detectors in the second position, wherein the second set of radiation detectors are positioned to detect the scattered gamma radiation.

7. A detector array comprising:

a plurality of radiation detectors, each pivotably mounted on a corresponding pivot for pivoting the corresponding radiation detector in a plurality of orientations for detecting gamma radiation from a target for generating corresponding detection signals for use in tomographic imaging of the target, said plurality including a first set of radiation detectors in a first position for detecting incident gamma radiation and for scattering the incident gamma radiation by Compton scattering; and a second set of radiation detectors in a second position, wherein the second set of radiation detectors are positioned to detect the scattered gamma radiation.

8. The detector array of claim 7 further comprising:

a base rotatable about an axis; and each of the plurality of radiation detectors is pivotably mounted to the base, wherein each radiation detector is pivoted to an angular orientation with respect to the axis for receiving the gamma radiation from a target aligned with the axis.

9. A method for tomographic imaging using a gamma camera comprising the steps of:

providing a plurality of radiation detectors of the gamma camera each mounted in an array;

moving each radiation detector in selectable orientations dependent upon a selected mode of operation;

wherein, in a first mode, the step of moving includes the step of moving the radiation detectors to corresponding positions with a first set of the radiation detectors generating Compton scattered gamma radiation and a second set of the radiation detectors detecting such Compton scattered radiation for performing Compton scatter tomography; and wherein, in a second mode, the step of moving includes the step of moving the radiation detectors about an axis of rotation for receiving radiation from a source aligned with the axis for performing single photon emission computed tomography (SPECT).

10. The method of claim 9 wherein, in a third mode, the step of moving includes the step of moving the radiation detectors about an axis of rotation with first and second sets of the radiation detectors in opposing orientations about a target aligned with the axis for performing positron emission tomography (PET).

11. The method of claim 9 wherein, in a third mode, the step of moving includes the step of moving the radiation detectors to a substantially planar orientation for performing conventional planar gamma radiation detection imaging.

12. The method of claim 9 further comprising, in the first mode, the steps of:

detecting incident gamma radiation at the first set of radiation detectors;

scattering the incident gamma radiation by Compton scattering to generate the Compton scattered radiation; and detecting the Compton scattered radiation at the second set of radiation detectors.

* * * * *